US010350152B2

(12) United States Patent
Bin et al.

(10) Patent No.: US 10,350,152 B2
(45) Date of Patent: Jul. 16, 2019

(54) SKIN WHITENING COMPOSITION, AND METHOD FOR SCREENING FOR MATERIALS HAVING SKIN WHITENING EFFECT

(71) Applicant: AMOREPACIFIC CORPORATION, Seoul (KR)

(72) Inventors: Bum-Ho Bin, Yongin-si (KR); Eun-Gyung Cho, Yongin-si (KR); Eun-Jeong Choi, Yongin-si (KR); Sungtae Kim, Yongin-si (KR); Suhyeon Choi, Yongin-si (KR); Taeryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/739,534

(22) PCT Filed: Jun. 15, 2016

(86) PCT No.: PCT/KR2016/006338
§ 371 (c)(1),
(2) Date: Dec. 22, 2017

(87) PCT Pub. No.: WO2017/003114
PCT Pub. Date: Jan. 5, 2017

(65) Prior Publication Data
US 2018/0177699 A1   Jun. 28, 2018

(30) Foreign Application Priority Data
Jun. 30, 2015  (KR) ........................ 10-2015-0093049

(51) Int. Cl.
| *A61K 8/49* | (2006.01) |
| *A61K 8/60* | (2006.01) |
| *A61K 8/73* | (2006.01) |
| *A61K 9/00* | (2006.01) |
| *A61K 9/06* | (2006.01) |
| *A61K 9/16* | (2006.01) |
| *A61K 9/20* | (2006.01) |
| *A61K 9/48* | (2006.01) |
| *A61K 31/18* | (2006.01) |
| *A61K 47/06* | (2006.01) |
| *A61K 47/10* | (2017.01) |
| *A61K 47/14* | (2017.01) |
| *A61K 47/22* | (2006.01) |
| *A61K 47/42* | (2017.01) |
| *A61Q 19/02* | (2006.01) |
| *G01N 33/50* | (2006.01) |
| *A61K 31/4178* | (2006.01) |

(52) U.S. Cl.
CPC ................ *A61K 8/494* (2013.01); *A61K 8/49* (2013.01); *A61K 8/4946* (2013.01); *A61K 8/60* (2013.01); *A61K 8/73* (2013.01); *A61K 9/0014* (2013.01); *A61K 9/0095* (2013.01); *A61K 9/06* (2013.01); *A61K 9/1652* (2013.01); *A61K 9/205* (2013.01); *A61K 9/4875* (2013.01); *A61K 31/18* (2013.01); *A61K 31/4178* (2013.01); *A61K 47/06* (2013.01); *A61K 47/10* (2013.01); *A61K 47/14* (2013.01); *A61K 47/22* (2013.01); *A61K 47/42* (2013.01); *A61Q 19/02* (2013.01); *G01N 33/5044* (2013.01)

(58) Field of Classification Search
CPC .... A61K 31/18; A61K 31/4178; A61K 47/06; A61K 47/10; A61K 47/14; A61K 47/22; A61K 47/42; A61K 8/49; A61K 8/494; A61K 8/4946; A61K 8/60; A61K 8/73; A61K 9/0014; A61K 9/0095; A61K 9/06; A61K 9/1652; A61K 9/205; A61K 9/4875; A61Q 19/02; G01N 33/5044
See application file for complete search history.

(56) References Cited

U.S. PATENT DOCUMENTS

| 2005/0020534 A1 | 1/2005 | Johnson, Jr. et al. |
| 2010/0104524 A1* | 4/2010 | Lee ..................... A61K 8/4973 424/62 |
| 2011/0189125 A1 | 8/2011 | George et al. |

FOREIGN PATENT DOCUMENTS

| JP | 06048935 A * | 2/1994 |
| KR | 10-0840144 B1 | 6/2008 |
| KR | 10-2014-0064272 A | 5/2014 |
| WO | 2014-018862 A1 | 1/2014 |

OTHER PUBLICATIONS

Murase et al (Journal of Biological Chemistry, Feb. 2009, vol. 284, pp. 4343-4353) (Year: 2009).*
Nakazawa et al (Journal of Investigative Dermatology, 1998, vol. 110, pp. 972-977) (Year: 1998).*
Clayton et al (Journal of Cell Science, 2005, vol. 118, pp. 3631-3638) (Year: 2005).*
Domingues et al (ImmunoTargets and Therapy, 2018, vol. 7, pp. 35-49) (Year: 2018).*
Khan et al (Cancer Biology and Therapy, online Dec. 2017, pp. 25-33) (Year: 2017).*
Strom et al (Nature Chemical Biology, 2006, vol. 2, pp. 474-479). (Year: 2006).*
International Search Report for PCT/KR2016/006338 (dated Sep. 13, 2016).

(Continued)

*Primary Examiner* — Mark V Stevens
(74) *Attorney, Agent, or Firm* — Merchant & Gould, P.C.

(57) ABSTRACT

Disclosed in the present specification are: a skin whitening composition having a skin whitening effect by controlling the secretion of exosomes to be secreted from melanocytes; and a method for screening for materials having a skin whitening effect. The skin whitening composition can promote apoptosis of melanocytes by inhibiting the amount of secretion of exosomes to be secreted from melanocytes, and consequently inhibits the generation of melanin through the apoptosis of melanocytes, thereby exhibiting a skin whitening effect.

2 Claims, 4 Drawing Sheets

(56) References Cited

OTHER PUBLICATIONS

Written Opinion for PCT/KR2016/006338 (dated Sep. 13, 2016).
Loyer et al., "Microvesicles as Cell—Cell Messengers in Cardiovascular Diseases," Circ. Res., 114:345-53 (2014).
Ohno et al., "Roles of exosomes and microvesicles in disease pathogenesis," Adv. Drug Deliv. Rev., 65:398-401 (2013).
Hornyak et al., "Mitf dosage as a primary determinant of melanocyte survival after ultraviolet irradiation," Pigment Cell Melanoma Res., 22(3):307-318 (2009).
Bahk et al., Proteomics, 4:3299-3307 (2004).
Zuo et al., "Towards global analysis of mammalian proteomes using sample prefractionation prior to narrow pH range two-dimensional gels and using one-dimensional gels for insoluble and large proteins," Electrophoresis, 22:1603-1615 (2001).

\* cited by examiner

SKIN WHITENING COMPOSITION, AND METHOD FOR SCREENING FOR MATERIALS HAVING SKIN WHITENING EFFECT

This application is a U.S. National Stage Application under 35 U.S.C. § 371 of International Patent Application No. PCT/KR2016/006338 filed Jun. 15, 2016, which claims the benefit of priority to Korean Patent Application No. 10-2015-0093049 filed Jun. 30, 2015, the disclosures of all of which are hereby incorporated by reference in their entireties. The International Application was published in Korean on Jan. 5, 2017 as WO 2017/003114.

TECHNICAL FIELD

Disclosed in the present specification are a skin whitening composition, and a method for screening for materials having a skin whitening effect.

BACKGROUND

Most animal cells have the ability to secrete extracellular vesicles of intracellular origin with various sizes and components, and these extracellular vesicles are found in all biological fluids including blood, urine, saliva, and cell culture fluids (Loyer X, Vion A C, Tedgui A, Boulanger C M, Microvesicles as cell-cell messengers in cardiovascular diseases, Circ Res 2014; 114: 345-53, Ohno S, Ishikawa A, Kuroda M. Roles of exosomes and microvesicles in disease pathogenesis. Adv Drug Deliv Rev 2013; 65: 398-401).

Extracellular vesicle is a membrane vesicle having a diameter of about 20 nm to about 5 μm, and is heterogeneous in its size and composition. They are classified into multiple different types including exosomes, ectosomes, microvesicles, microparticles, apoptotic bodies, etc.

Extracellular vesicle reflects the state of the secreting cells (donor cells), exhibits various biological activities depending on the type of the secreting cells, and plays an important role in intercellular interactions by transferring genetic materials and proteins between cells.

Melanin is a phenol-based biopolymer in the form of a complex of black pigment and protein. It is found in browning, which occurs when a cut surface of an apple, a potato, or a banana is exposed to air, or in the outer feathers, skin, head, eyes, etc. of animals. When melanin is overproduced, it is deposited on the skin to form spots and freckles, promote skin aging, and may even cause skin cancer.

Melanocytes in the human body are cells synthesizing melanin as a part of defense mechanism against ultraviolet rays from the outside. They prevent apoptosis of the skin due to ultraviolet rays. When the skin is exposed to ultraviolet rays from the outside, melanocytes among skin tissue cells react with ultraviolet rays to synthesize melanin.

The mechanism of the synthesis of melanin by ultraviolet rays is as follows: Melanin stimulating hormone (MSH) is secreted due to ultraviolet rays and MSH responds to the receptor MC1R to increase cAMP in melanocytes, which induces the reaction of genes for melanin synthesis, resulting in the synthesis of melanin. The synthesized melanin is secreted out of the melanocytes to protect the skin from ultraviolet rays. Proteins involved in the biosynthesis of melanin include mitf, tyr, trp1, and trp2.

However, there has been no report on the relationship between the amount of secretion of exosomes secreted from melanocytes and apoptosis of melanocytes. Prior art relating to a method for screening for materials having whitening activities is described in Korean Patent No. 10-0840144.

CITATION LIST

Patent Literature

[Patent Literature 1]
Korean Patent No. 10-0840144.

SUMMARY OF INVENTION

Technical Problem

In one aspect, the objective of the present specification is to provide a composition having a skin whitening effect by controlling the release of exosomes from melanocytes.

In another aspect, the objective of the present specification is to provide a method for screening for materials having a skin whitening effect by identifying the amount of secretion of exosomes secreted from melanocytes.

Solution to Problem

In one aspect, the technology disclosed in the present specification provides a skin whitening composition comprising, as an active ingredient, an exosome inhibitor that inhibits the amount of secretion of exosomes to be secreted from melanocytes.

In one exemplary embodiment, the exosome inhibitor may be one or more selected from the group consisting of GW4869 and pifithrin-μ.

In one exemplary embodiment, the active ingredient may be one that inhibits the generation of melanin.

In one exemplary embodiment, the active ingredient may be one that prevents, improves, or treats one or more skin pigmentation diseases selected from the group consisting of spots, freckles, lentigo, nevus, melanoma, drug-induced pigmentation, post-inflammatory pigmentation, and dermatitis-induced pigmentation.

In another aspect, the technology disclosed in the present specification provides a method for enhancing skin whitening, comprising the step of applying to a subject an effective amount of a composition comprising an exosome inhibitor.

In another aspect, there is provided a method for the prevention, improvement, or treatment of diseases caused by overproduction of melanin, comprising the step of administering a composition comprising an exosome inhibitor in an amount effective for the prevention, improvement, or treatment of diseases caused by overproduction of melanin, to a subject in need thereof.

In one exemplary embodiment, the method may comprise the step of applying the composition in the form of a pharmaceutical composition, a cosmetic composition or a food composition.

In one exemplary embodiment, the method may comprise the step of applying the composition to the skin of a subject.

In another aspect, the technology disclosed in the present specification provides an exosome inhibitor for enhancing the whitening of the skin of a subject.

In another aspect, the technology disclosed in the present specification provides an exosome inhibitor for the prevention, improvement, or treatment of diseases caused by overproduction of melanin.

In another aspect, the technology disclosed in the present specification provides a method for screening for materials having a skin whitening effect comprising the steps of:

treating melanocytes with a test material and then irradiating ultraviolet rays on them, or irradiating ultraviolet rays on melanocytes and then treating them with a test material; and identifying the relative amount of secretion of exosomes secreted from the melanocytes.

In one exemplary embodiment, the relative amount of secretion of exosomes may be identified based on the comparison with the amount of secretion of exosomes secreted from melanocytes as a control, wherein the control is melanocytes irradiated with ultraviolet rays without being treated with a test material.

In one exemplary embodiment, the method of the present invention may comprise the step of, after identifying the relative amount of secretion of exosomes, selecting the test material that has reduced the relative amount of secretion of exosomes as a material having a skin whitening effect.

In one exemplary embodiment, the ultraviolet irradiation may be performed by irradiating UVB at 20 to 30 mJ/cm$^2$.

In one exemplary embodiment, the time for treatment of melanocytes with a test material may be 10 to 24 hours.

In one exemplary embodiment, the amount of secretion of exosomes may be identified from the amount of expression of CD81 or HSP90.

In another aspect, the technology disclosed in the present specification provides a skin whitening composition comprising, as an active ingredient, a material selected as a material having a skin whitening effect according to the above method.

Advantageous Effects of Invention

In one aspect, the technology disclosed in the present specification provides a composition having a skin whitening effect by controlling the release of exosomes from melanocytes.

In another aspect, the technology disclosed in the present specification provides a method for screening for materials having a skin whitening effect by identifying the amount of secretion of exosomes secreted from melanocytes.

DESCRIPTION OF EMBODIMENTS

Embodiments

Hereinafter, the present invention will be described in detail.

In one aspect, the technology disclosed in the present specification provides a skin whitening composition comprising, as an active ingredient, an exosome inhibitor that inhibits the amount of secretion of exosomes to be secreted from melanocytes.

As used herein, the term "exosome" refers to a nano-sized extracellular vesicle secreted from a cell and released into the extracellular space. Exosome is a membrane vesicle in which the inside and the outside are separated from each other, and is known to perform various functions, including binding to other cells and tissues to transfer membrane components, proteins (growth hormone, cytokine, etc.), RNA, etc. to them and thereby mediating intercellular communication. Meanwhile, cells surrounding a melanocyte and intercellular materials exist around the melanocyte. Specifically, intercellular materials such as keratinocyte or fibroblast and/or collagen may exist within a certain radius, for example, within 2 mm from the melanocyte. Melanocyte secretes exosomes into the extracellular matrix.

In one aspect, the exosome may be an extracellular vesicle with a diameter of 20 to 400 nm.

As used herein, the term "exosome inhibitor" refers to a material that inhibits the amount of secretion of exosomes secreted from melanocytes. It has the broadest meaning of the term, which covers a material that inhibits the formation of exosomes in melanocytes or the secretion or release of exosomes from melanocytes.

In one exemplary embodiment, the exosome inhibitor may be one or more selected from the group consisting of GW4869 and pifithrin-μ.

"GW4869" is a sphingomyelinase (Smase) inhibitor having the molecular formula $C_{30}H_{30}Cl_2N_6O_2$ and represented by Formula 1 below (CAS 6823-69-4). Sphingomyelinase is a sphingomyelin-specific phospholipase C that hydrolyzes sphingomyelin to produce ceramide and phosphocholine.

[Formula 1]

"pifithrin-μ" is a p53 inhibitor having the molecular formula $C_8H_7NO_2S$ and is represented by Formula 2 (CAS 64984-31-2). p53 is a cancer-controlling gene that controls cells to prevent unnecessary proliferation of the cells. However, abnormal activation of p53 is fatal to cell survival. Pifithrin has been identified as a compound that promotes apoptosis of cancer cells while protecting normal cells during radiation therapy.

[Formula 2]

In one exemplary embodiment, the active ingredient has the effect of preventing, treating or improving skin damage or skin diseases that are directly or indirectly associated with the increase of melanocytes. That is, the active ingredient effectively inhibits the generation of melanin and thus has the effect of preventing, treating or improving diseases caused by overproduction of melanin.

The diseases caused by overproduction of melanin may be one or more selected from the group consisting of spots, freckles, age spots, blemishes, epidermal melanocytic lesion, cafe's au lait macules, Becker's nevus, nevus spilus, lentigines, dermal melanocytic lesions, mongolian spot, nevus of Ota, acquired bilateral nevus of Ota-like macules, nevus of Ito, blue nevus, melanocytic nevus, junctional nevus, compound nevus, intradermal nevus, halo nevus, congenital nevocytic nevus, Spitz nevus, dysplastic nevus, melanoma, lentigo maligna melanoma, superficial spreading melanoma, acral lentiginous melanoma, nodular melanoma, pigment basal cell carcinoma, dermatofibromas, dermoid cyst, keloid and keratoacanthomas.

In one exemplary embodiment, the composition may be one that prevents, improves, or treats one or more skin pigmentation diseases selected from the group consisting of spots, freckles, lentigo, nevus, and melanoma, which occur locally on the skin due to increased melanin generation, drug-induced pigmentation, post-inflammatory pigmentation, and dermatitis-induced pigmentation.

In another aspect, the technology disclosed in the present specification provides a method for screening for materials having a skin whitening effect, comprising the steps of: treating melanocytes with a test material and then irradiating ultraviolet rays on them, or irradiating ultraviolet rays on melanocytes and then treating them with a test material; and identifying the relative amount of secretion of exosomes secreted from the melanocytes.

In one exemplary embodiment, the relative amount of secretion of exosomes may be identified based on the comparison with the amount of secretion of exosomes secreted from melanocytes as a control, wherein the control is melanocytes irradiated with ultraviolet rays without being treated with a test material.

In one exemplary embodiment, the method of the present invention may comprise the step of, after identifying the relative amount of secretion of exosomes, selecting the test material that has reduced the relative amount of secretion of exosomes as a material having a skin whitening effect.

In one exemplary embodiment, the ultraviolet irradiation may be performed by irradiating UVB at 20 to 30 mJ/cm$^2$.

In one exemplary embodiment, the time for treatment of melanocytes with a test material may be 10 to 24 hours.

In one exemplary embodiment, the amount of secretion of exosomes may be identified, for example, by counting the number of particles of exosomes isolated from the same number of cells by the same isolation method, using a quantitative analysis instrument Q-Nano or NanoSight according to nanoparticle tracking analysis (NTA), or by quantifying protein and lipid on the surface of exosomes or protein, peptide, RNA, miRNA (microRNA), lncRNA (long noncoding RNA), metabolites, etc. within exosomes. Depending on the subject to be quantified, the quantification method may be suitably selected by a person skilled in the art from western blot, dot blot, ELISA, northern blot, PCR, RT-qPCR, GC-MS, LC-MS, NMR, radioimmunoassay, immunoprecipitation assay, radioimmunodiffusion, FACS, protein chip, etc. For example, in the examples of the present specification, the amount of exosome was evaluated based on visual comparison of CD81 on the surfaces of exosomes or HSP90 within exosomes as a quantitative marker through western blot, but the present invention is not limited thereto.

The exosomes secreted from melanocytes into the extracellular matrix inhibit the apoptosis of ultraviolet-irradiated melanocytes. Therefore, it is possible to promote apoptosis of melanocytes by inhibiting the amount of secretion of exosomes to be secreted from melanocytes. The apoptosis of melanocytes consequently inhibits the generation of melanin, leading to a skin whitening effect (Pigment Cell Melanoma Res. 2009 June; 22(3):307-318).

In addition, a material that inhibits or promotes the secretion of exosomes from melanocytes can control the generation of melanin by promoting (secretion-inhibiting material) or inhibiting (secretion-promoting material) the apoptosis of melanocytes. Thus, it is possible to screen for a material that controls skin pigmentation by treating melanocytes with a candidate material having a skin whitening effect before or after treatment with ultraviolet rays and identifying the amount of secretion of exosomes secreted from the melanocytes.

In another aspect, the technology disclosed in the present specification provides a skin whitening composition comprising, as an active ingredient, a material selected as a material having a skin whitening effect according to the above method.

According to one exemplary embodiment, the composition may be a pharmaceutical composition.

The pharmaceutical composition may further contain, in addition to the exosome inhibitor, a pharmaceutical adjuvant such as a preservative, a stabilizer, a hydrating agent or an emulsification promoter, a salt and/or buffer for controlling osmotic pressure, and other therapeutically useful materials. It may be formulated into various formulations for oral or parenteral administration according to a common method.

Formulations for oral administration include, for example, tablets, pills, hard and soft capsules, liquids, suspensions, emulsions, syrups, powders, dusts, granules, pellets, etc. These formulations may comprise, in addition to the active ingredient, a surfactant, a diluent (e.g., lactose, dextrose, sucrose, mannitol, sorbitol, cellulose and glycine) or a lubricant (e.g., silica, talc, stearic acid and magnesium or calcium salt thereof and polyethylene glycol). The tablet may comprise a binder such as magnesium aluminum silicate, starch paste, gelatin, tragacanth, methyl cellulose, sodium carboxymethyl cellulose and polyvinylpyrrolidine, and optionally may comprise a pharmaceutical additive such as a disintegrant, e.g. starch, agar, alginic acid or a sodium salt thereof, an absorbent, a colorant, a flavoring agent, a sweetener, etc. The tablet may be prepared according to a common mixing, granulation or coating method.

The formulation for parenteral administration may be a transdermal formulation, for example, injections, drops, ointments, lotions, gels, creams, sprays, suspensions, emulsions, suppositories, patches, etc., although not limited thereto.

The pharmaceutical composition may be administered parenterally, rectally, topically, transdermally, subcutaneously, etc.

The determination of the dose of the active ingredient is within the knowledge of those skilled in the art. The daily dose of the drug will vary depending on various factors such as the progress and the time at onset of the disease, age, health condition of the subject, complications, etc. However, in one aspect, the dose for adults may be 1 μg/kg to 200 mg/kg of the composition in one to three divided doses per day. In another aspect, it may be 50 μg/kg to 50 mg/kg of the composition in one to three divided doses per day. The dose does not limit the scope of the present disclosure by any means.

The pharmaceutical composition may be a preparation for external application to skin. The preparation for external application to skin encompasses any substance applied on the skin and may include medicines in the form of various formulations.

According to one exemplary embodiment, the composition may be a cosmetic composition.

The cosmetic composition may further include, in addition to the exosome inhibitor, a functional additive and an ingredient contained in general cosmetic compositions. The functional additive may be any one selected from the group consisting of water-soluble vitamins, oil-soluble vitamins, polypeptides, polysaccharides, sphingolipids and seaweed extracts. Other ingredients that may be included in the composition include oil and fat, a humectant, an emollient, a surfactant, an organic or inorganic pigment, an organic powder, a UV absorbent, a preservative, a sterilizer, an antioxidant, a plant extract, a pH control agent, an alcohol, a colorant, a fragrance, a blood circulation stimulant, a cooling agent, an antiperspirant, purified water, etc.

The formulation of the cosmetic composition is not particularly limited and may be appropriately selected according to the purpose. For example, it may be formulated into one more selected from the group consisting of skin lotions, skin softeners, skin toners, astringents, lotions, milk lotions, moisturizing lotions, nourishing lotions, massage creams, nourishing creams, moisturizing creams, hand creams, foundations, essences, nourishing essences, packs, soaps, cleansing foams, cleansing lotions, cleansing creams, body lotions and body cleansers, although not limited thereto.

When the formulation of the present invention is a paste, a cream or a gel, an animal fiber, a vegetable fiber, wax, paraffin, starch, tragacanth, a cellulose derivative, polyethylene glycol, silicone, bentonite, silica, talc, or zinc oxide, etc. may be used as a carrier.

When the formulation of the present invention is a powder or a spray, lactose, talc, silica, aluminum hydroxide, calcium silicate or polyamide powder may be used as a carrier. In particular, when the formulation is a spray, it may further comprise a propellent such as chlorofluorohydrocarbon, propane/butane or dimethyl ether.

When the formulation of the present invention is a solution or an emulsion, a solvent, a dissolving agent or an emulsifier is used as a carrier. Examples thereof include water, ethanol, isopropanol, ethyl carbonate, ethyl acetate, benzyl alcohol, benzyl benzoate, propylene glycol, 1,3-butylene glycol, glycerol aliphatic ester, polyethylene glycol or fatty acid ester of sorbitan.

When the formulation of the present invention is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, or tragacanth, etc. may be used as a carrier.

When the formulation of the present invention is a surfactant-containing cleansing, aliphatic alcohol sulfate, aliphatic alcohol ether sulfate, sulfosuccinic acid monoester, isethionate, imidazolium derivative, methyltaurate, sarcosinate, fatty acid amide ether sulfate, alkylamido betaine, aliphatic alcohol, fatty acid glyceride, fatty acid diethanolamide, a vegetable oil, a linolin derivative or ethoxylated glycerol fatty acid ester may be used as a carrier.

According to one exemplary embodiment, the composition may be a food composition.

The food composition may be in the form of a liquid or solid formulation. For example, it may be in the form of various foods, beverage, gum, tea, vitamin complex, health supplement, etc. It may be in the form of powder, granule, tablet, capsule or beverage. The food composition in the form of each formulation may further include, in addition to the active ingredient, an ingredient commonly used in the pertinent field. The ingredient may be selected and added without difficulty by those skilled in the art according to the desired formulation or purpose. The addition of other ingredient may give a synergic effect.

There are no particular limitations on the liquid ingredients that may be contained in addition to the active ingredient disclosed in the present specification. It may comprise various flavoring agents or natural carbohydrates as additional ingredients, as do common beverages. Examples of natural carbohydrates are conventional sugars such as monosaccharide, disaccharides such as glucose and fructose, polysaccharides such as maltose and sucrose, dextrin, cyclodextrin, etc. and sugar alcohols such as xylitol, sorbitol, erythritol, etc. Also, natural flavoring agents (thaumatin, stevia extract (e.g., rebaudioside A, glycyrrhizin, etc.) and synthetic flavoring agents (e.g., saccharin, aspartame, etc.) may be advantageously used as the flavoring agent. In general, the natural carbohydrate may be included in an amount of about 1 to 20 g, and in one aspect, about 5 to 12 g per 100 ml of the composition disclosed in the present specification.

In one aspect, the food composition may comprise various nutrients, a vitamin, a mineral (electrolyte), flavoring agents such as a synthetic flavoring agent and a natural flavoring agent, a coloring agent and an improving agent (cheese, chocolate, etc.), pectic acid or a salt thereof, alginic acid or a salt thereof, an organic acid, a protective colloidal thickening agent, a pH controlling agent, a stabilizing agent, a preservative, glycerin, alcohol, a carbonating agent as used in carbonated beverages, etc. In another aspect, it may comprise fruit flesh for the production of natural fruit juices and vegetable beverages. These ingredients may be used alone or as a mixture thereof. The proportion of the additive may vary, however, generally it is 0.001 to about 20 parts by weight with respect to 100 parts by weight of the composition disclosed in the present specification.

Examples

Hereinafter, the present invention will be described in detail by way of examples. It will be apparent to those skilled in the art that these examples are for illustrative purposes only, and the scope of the present invention is not construed as being limited by these examples.

Test Example (1) Cell Culture and Materials

Normal human melanocytes (Cascade Biologics, Portland, Oreg., USA) were kept in M-254 medium (Cascade) containing a human melanocyte growth supplement (Cascade). GW4869 (Santa Cruz Biotechnology, Santa Cruz, Calif., USA) and pifithrin-µ (Sigma, St. Louis, Mo., USA) were dissolved in DMSO for use.

(2) Isolation of Exosomes

For isolation of exosomes, confluent melanocytes were washed with PBS and cultured in M-254 for 48 hours. Conditioned medium was collected and centrifuged at 500×g for 10 minutes, 3,000×g for 20 minutes, and 100,000×g for 2 hours. The resultant exosome-containing pellet was resuspended in PBS and stored at −80° C. Also, conditioned medium was purified by filtration through a 0.45 μm pore filter (Millipore, Billerica, Mass., USA) and concentrated using a 100 kDa cut-off spin column (Millipore). Exosomes were isolated using the ExoQuick-TC kit (SBI, San Jose, Calif., USA) according to the manufacturer's instructions. 20 μl of isolated exosomes were analyzed by western blot and silver staining.

(3) Dynamic Light Scattering (DLS) Analysis

The diameter of exosome was measured using a Zetasizer Nano S instrument (Malvern Instruments Ltd., Worcestershire, UK) equipped with a 633 nm laser at a scattering intensity of 10×30 s.

(4) In-Gel Protein Digestion

Exosome proteins were digested by SDS-PAGE. The SDS-PAGE gel was cut into 10 slices and subjected to in-gel digestion with trypsin by a known method (Batik Y Y, Kim S A, Kim J S, et al. (2004) Antigens secreted from Mycobacterium tuberculosis: identification by proteomics approach and test for diagnostic marker. Proteomics 4:3299-307). Briefly, the gel slices were washed 4-5 times with 1:1 acetonitrile (ACN)/25 mM ammonium bicarbonate (ABC), dehydrated in 100% ACN, and dried. After reduction in 10 mM DTT with 100 mM ABC at 56° C. for 45 minutes and alkylation in 55 mM iodoacetamide with 100 mM ABC at room temperature for 30 minutes in the dark, the slices were dried in 100% ACN and rehydrated in 325 mM ABC containing 20 ng of trypsin at 37° C. for 20 hours. The liquid was transferred to a new tube, and the remaining peptides were extracted from the gel with 50% (v/v) aqueous acetonitrile containing 0.1% (v/v) formic acid at 30° C. for 40 minutes. The combined supernatants were evaporated, and dissolved in 5% (v/v) aqueous acetonitrile solution containing 0.1% (v/v) formic acid for mass spectrometry.

(5) Identification of Proteins by LC-MS/MS

The digested peptides were analyzed using reversed-phase capillary HPLC directly coupled to a Finnigan LCQ ion-trap mass spectrometer (LC-MS/MS) according to a known method (Zuo X, Echan L, Hembach P, et al. (2001) Towards global analysis of mammalian proteomes using sample prefractionation prior to narrow pH range two-dimensional gels and using one-dimensional gels for insoluble and large proteins. Electrophoresis 22:1603-15), with slight modifications. The peptides were bound to the trapping column for 10 minutes and eluted with a gradient of 5-80% (v/v) aqueous acetonitrile containing 0.1% (v/v) formic acid at a flow rate of 0.2 μl/min for 50 minutes. Tandem MS was performed at m/z=450-2000 Da, and individual spectrum was processed using TurboSEQUEST software (Thermo Quest, San Jose, Calif.). The obtained peak lists were used to query the MSDB or NCBI databases using the MASCOT program (http://www.matrixscience.com).

(6) Western Blot and Silver Staining

Cells or isolated exosomes were lysed with lysis buffer (1% NP-40, 0.05 M Tris-HCl, pH 7.5, 0.15 M NaCl, and 0.01 M $MgCl_2$) containing protease inhibitors (Sigma). Protein concentrations were determined using BCA assays, and samples were digested by SDS-PAGE, transferred to a PVDF membrane, and probed with antibodies against CD81 (SBI). For silver staining, SDS-PAGE gels were subjected to a silver stain kit (Thermo Fisher Scientific, Rockford, Ill., USA) according to the manufacturer's instructions.

(7) Cytotoxicity Test

Melanocytes were seeded in a 6-well plate at a density of $1\times10^4$ cells/well. The next day, 10 μl of exosomes isolated from the same number of cells were treated. Cells were fixed with 4% formaldehyde in PBS for 15 minutes, washed with PBS and stained with 0.1% crystal violet for 20 minutes. After washing with PBS, the cells were dried and lysed with 10% acetic acid. The absorbance was measured at 590 nm using a spectrophotometer.

(8) Quantitative Real-Time PCR

Total RNA was isolated using Trizol reagent (Invitrogen) and was reverse-transcribed into cDNA using ReverTra Ace (Toyobo, Osaka, Japan). Gene expression analysis was performed using TaqMan Universal Master Mix and TaqMan Gene Expression Assays: Hs00365052_m1 (Applied Biosystems, Foster City, Calif., USA).

(9) Statistical Analysis

Two-tailed Student's t-tests were used to analyze differences between two groups. The data are presented as the mean±SD of three experiments (*: $p<0.005$, : $p<0.05$)

Test Results 1: Identification of Exosomes Secreted from Melanocytes

Figure 1:
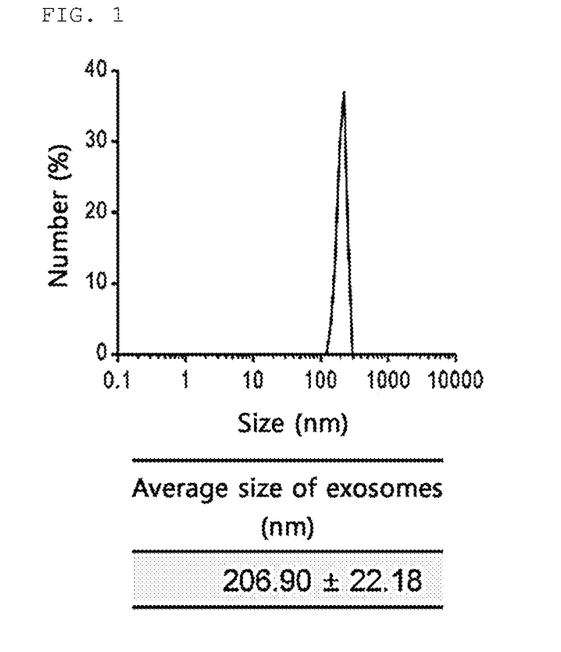
FIG. 1 illustrates the results of one test example of the present specification identifying the average size of exosomes released from melanocytes.

Melanocytes secreted and released exosomes. The analysis (dynamic light scattering analysis) of the size of the isolated exosomes showed that exosomes released from melanocytes have an average diameter of 206.90±22.18 nm (See FIG. 1).

Test Results 2: Changes in the Amount of Secretion of Exosomes Secreted from Melanocytes Due to Ultraviolet Irradiation Melanocytes were irradiated with UVB (20 $mJ/cm^2$) and cultured for 24 hours. The result showed that the amount of secretion of exosomes increased upon exposure to ultraviolet rays.

Figure 2A:
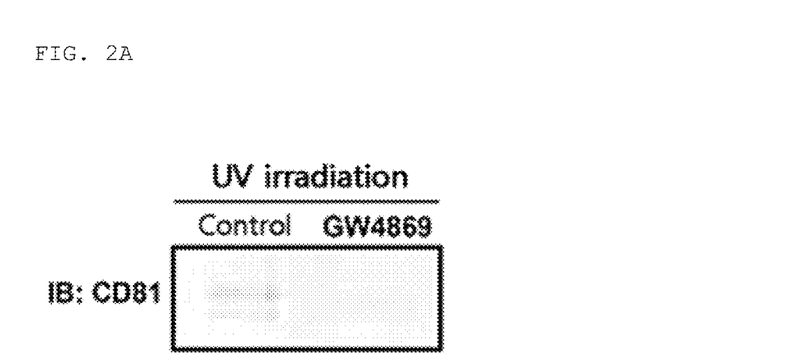
FIGS. 2A and 2B show the results of one test example of the present specification demonstrating that the amount of secretion of exosomes, which increased upon irradiation with ultraviolet rays, decreased when treated with an exosome inhibitor.
Figure 2B:
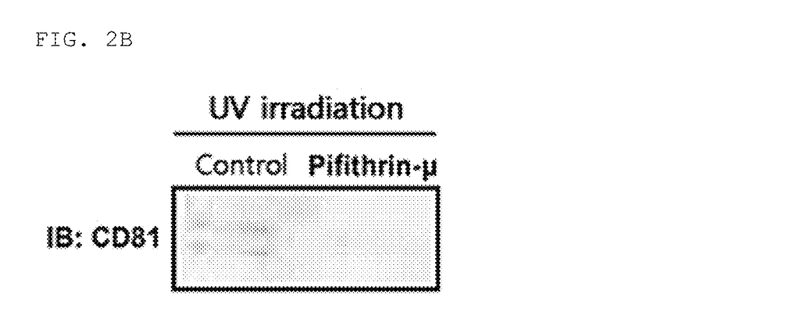

Also, when treated with 10 μM GW4869 (Smase (sphingomyelinase) inhibitor) or 10 μM pifithrin-μ (p53 inhibitor), which are exosome generation/secretion inhibitors, for 12 hours before UVB exposure, the amount of expression of the exosome marker CD81 decreased (see FIGS. 2A and 2B).

The results show that the amount of release of exosomes increases upon exposure to ultraviolet rays, and that the amount of release of exosomes decreases despite exposure to ultraviolet rays, when an exosome generation/secretion inhibitor is added.

Figure 3:
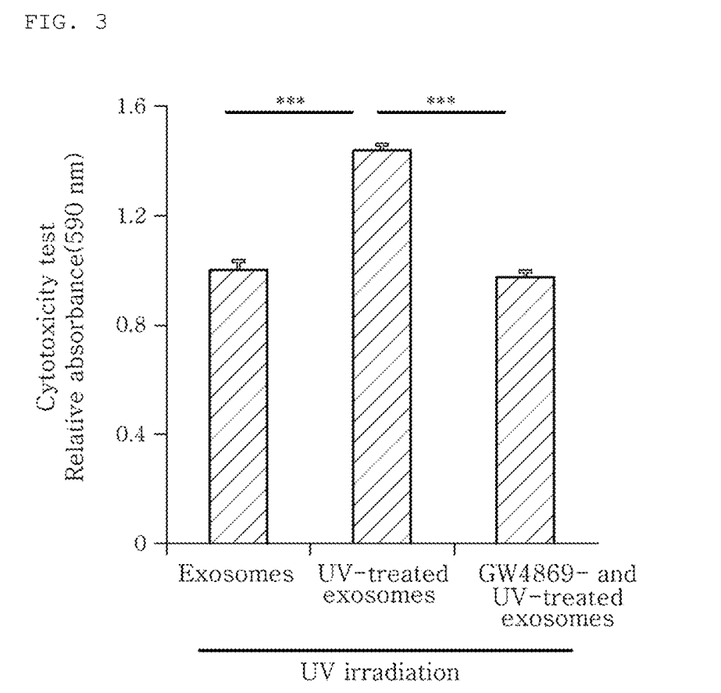
FIG. 3 shows the results of one test example of the present specification demonstrating the effect of the exosome inhibitor on the viability of ultraviolet-irradiated melanocytes.
Figure 4:
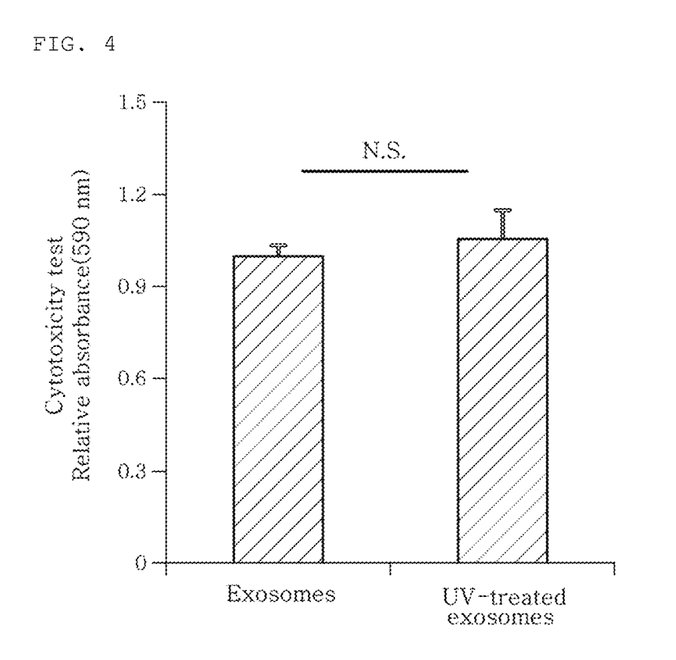
FIG. 4 shows the results of one test example of the present specification demonstrating that there was no significant difference in cell viability depending on exosomes, in UVB-nonirradiated melanocytes.

Test Results 3: Effects of Exosome Inhibitor on the Viability of Ultraviolet-Irradiated Melanocytes Each of the exosomes obtained from UVB-untreated melanocytes, UVB-treated melanocytes, or UVB- and GW4869-treated melanocytes, together with melanocytes, were irradiated with UVB (20 $mJ/cm^2$), and cultured for 3 days. As a result, it was found that the exosomes derived from melanocytes exposed to ultraviolet rays increased the viability of ultraviolet-damaged melanocytes, as shown in FIG. 3. The exosomes derived from melanocytes treated with ultraviolet rays together with GW4869 and pifithrin-μ, which are materials that inhibit the secretion of exosomes, showed a reduced effect in the enhancement of the viability of melanocytes. Meanwhile, when each of the exosomes obtained from UVB-untreated melanocytes or UVB-treated melanocytes were cultured together with melanocytes in the same manner as above, but without irradiation of UVB on melanocytes, it was found that there was no significant difference in the viability of melanocytes between the exosomes (see FIG. 4).

The results show that exosomes derived from melanocytes exposed to ultraviolet rays increase the viability of ultraviolet-damaged melanocytes, and that exosomes released from melanocytes upon UV irradiation inhibits the apoptosis of melanocytes.

Thus, it was confirmed that a material that inhibits or promotes the release of exosomes from melanocytes can control the generation of melanin by promoting (release-inhibiting material) or inhibiting (release-promoting material) the apoptosis of melanocytes.

Formulation examples of the composition according to one aspect of the present invention are described below, but other formulations may also be employed. The formulation examples are for illustrative purposes only and not intended to limit the scope of the present invention.

Formulation Example 1: Soft Capsule 50 mg of GW4869 or pifithrin-μ, 80-140 mg of L-carnitine, 180 mg of soybean oil, 2 mg of palm oil, 8 mg of hydrogenated vegetable oil, 4 mg of yellow wax and 6 mg of lecithin were mixed. Then, a soft capsule was prepared by filling 400 mg of the mixture per capsule.

Formulation Example 2: Tablet 50 mg of GW4869 or pifithrin-μ, 200 mg of galactooligosaccharide, 60 mg of lactose and 140 mg of maltose were mixed and granulated using a fluidized bed dryer. Then, after adding 6 mg of sugar ester, the mixture was compressed by a tablet machine to prepare a tablet.

Formulation Example 3: Granule 50 mg of GW4869 or pifithrin-μ, 250 mg of anhydrous crystalline glucose and 550 mg of starch were mixed and granulated using a fluidized bed dryer. The resultant granules were filled in a pouch.

Formulation Example 4: Drink 50 mg of GW4869 or pifithrin-μ, 10 g of glucose, 0.6 g of citric acid, and 25 g of liquid oligosaccharide were mixed, and 300 ml of purified water was added. 200 mL of the mixture was filled in a bottle and sterilized at 130° C. for 4-5 seconds to prepare a drink.

Formulation Example 5: Lotion

A lotion was prepared according to a commonly employed method with the composition described in Table 1 below.

TABLE 1

| Ingredient | Content (wt %) |
| --- | --- |
| GW4869 or pifithrin-μ | 2.00 |
| L-ascorbic acid-2-phosphate magnesium salt | 1.00 |
| Water-soluble collagen (1% aqueous solution) | 1.00 |
| Sodium citrate | 0.10 |
| Citric acid | 0.05 |
| Licorice extract | 0.20 |
| 1,3-butylene glycol | 3.00 |
| Purified water | balance |
| Total | 100.00 |

Formulation Example 6: Cream

A cream was prepared according to a commonly employed method with the composition described in Table 2 below.

TABLE 2

| Ingredient | Content (wt %) |
| --- | --- |
| GW4869 or pifithrin-μ | 2.00 |
| Polyethylene glycol monostearate | 2.00 |
| Self-emulsifying glyceryl monostearate | 5.00 |
| Cetyl alcohol | 4.00 |
| Squalene | 6.00 |
| Tri-2-ethylhexane glyceryl | 6.00 |
| Sphingoglycolipids | 1.00 |
| 1,3-butylene glycol | 7.00 |
| Purified water | balance |
| Total | 100.00 |

Formulation Example 7: Pack

A pack was prepared according to a commonly employed method with the composition described in Table 3 below.

TABLE 3

| Ingredient | Content (wt %) |
| --- | --- |
| GW4869 or pifithrin-μ | 2.00 |
| Polyvinyl alcohol | 13.00 |
| L-ascorbic acid-2-phosphate magnesium salt | 1.00 |
| Lauroylhydroxyproline | 1.00 |
| Water-soluble collagen (1% aqueous solution) | 2.00 |
| 1,3-butylene glycol | 3.00 |
| Ethanol | 5.00 |
| Purified water | balance |
| Total | 100.00 |

Although specific embodiments of the present invention are described in detail as described above, it will be apparent to those skilled in the art that the specific description describes merely desirable embodiments and should not be construed as limiting the scope of the present invention. Therefore, the substantial scope of the present invention is defined by the accompanying claims and equivalents thereof.

We claim:

1. A method for skin whitening, comprising administering an effective amount of an exosome inhibitor to a subject in need thereof, wherein the exosome inhibitor is GW4869.

2. The method for skin whitening according to claim 1, wherein the exosome inhibitor whitens skin pigmentation in one or more skin pigmentation diseases, wherein the one or more skin pigmentation diseases are selected from the group consisting of spots, freckles, lentigo, nevus, melanoma, drug-induced pigmentation, post-inflammatory pigmentation, and dermatitis-induced pigmentation.

* * * * *